United States Patent [19]

Lee

[11] Patent Number: 5,024,934
[45] Date of Patent: Jun. 18, 1991

[54] DETECTION OF MINIMAL NUMBERS OF NEOPLASTIC CELLS CARRYING DNA TRANSLOCATIONS BY DNA SEQUENCE AMPLIFICATION

[75] Inventor: Ming-Sheng Lee, Houston, Tex.

[73] Assignee: The Board of Regents, The University of Texas System, Austin, Tex.

[21] Appl. No.: 167,585

[22] Filed: Mar. 14, 1988

[51] Int. Cl.⁵ .................. C12Q 1/68; C07H 15/12; C12N 15/00
[52] U.S. Cl. ........................................ 435/6; 536/27; 935/77; 935/78
[58] Field of Search ............... 435/6; 536/27; 935/77, 935/78

[56] References Cited

U.S. PATENT DOCUMENTS 4,683,202  7/1987  Mullis .................................. 435/91

FOREIGN PATENT DOCUMENTS

A0236069  9/1987  European Pat. Off. .

OTHER PUBLICATIONS

International Search Report, Appl. No. PCT/US 89/00843, International Filing Date Mar. 2, 1989, Priority Date Claimed Mar. 14, 1988.
Crescenzi et al., Proc. Natl. Acad. Sci. USA, vol. 85, pp. 4869-4873, Jul. 1988, "Thermostable DNA Polymerase Chain Amplification of t(14;18) Chromosome Breakpoints and Detection of Minimal Residual Disease".
Stetler-Stevenson et al., Chemical Abstracts, vol. 110, No. 3, 147, Abstract No. 19393s, "Detection of Occult Follicular Lymphoma by Specific DNA Amplification".
Raffeld et al., Chemical Abstracts, vol. 107, No. 5, 186, Aug. 3, 1987, Abstract No. 34198p, "Clonal Evolution of t(14;18) Follicular Lymphomas Demonstrated by Immunoglobulin Genes and the 18q21 Major Breakpoint Reg.".
Raffeld, et al., Cancer Res., vol. 47, pp. 2537-2542 (1987), "Clonal Evolution of t(14;18) Follicular Lymphomas Demonstrated by Immunoglobulin Genes and the 18q21 Major Breakpoint Region".
Stetler-Stevenson, M. et al., Blood, vol. 72, "Detection of Occult Follicular Lymphoma by Specific DNA Amplification", pp. 1822-1825 (1988).
Weiss et al, New England Journal of Medicine, vol. 317, No. 19, Nov. 5, 1987, pp. 1185-1189.
Tsujimoto et al, Science, vol. 229, Sep. 27, 1985, pp. 1390-1393.
Hu et al, Detection of B-Cell Lymphoma in Peripheral Blood by DNA Hybridisation, The Lancet, Nov. 16, 1985, pp. 1092-1095.
Cleary et al., Immunoglobulin Gene Rearrangement as a Diagnostic Criterion of B-cell Lymphoma, Proc. Natl. Acad. Sci., USA, vol. 81, pp. 593-597.
Saiki et al., Enzymatic Amplification of B-Globin Genomic Sequences and Restriction Site Analysis for Diagnosis of SickleCell Anemia, Science, vol. 230, Dec. 1985, pp. 1350-1354.

(List continued on next page.)

Primary Examiner—Robert A. Wax
Assistant Examiner—Mindy B. Fleisher
Attorney, Agent, or Firm—Arnold, White & Durkee

[57] ABSTRACT

The present invention related to a sensitive method of detecting t(14;18) translocations arising from variable breakpoints in the J-region of the immunoglobulin heavy chain locus on chromosome 14. These breakpoints are typical abnormalities of human follicular lymphomas. In particular, the invention utilizes a sequence amplification by polymerase chain reaction in which primers are synthesized which are so designed that one primer will always flank the breakpoint in the J-region regardless of variation in the breakpoint. Consequently, the invention is a highly sensitive tool to detect minimal residual cells carrying the t(14;18) and has potential to identify patients with subclinical disease.

26 Claims, 4 Drawing Sheets

OTHER PUBLICATIONS

Lee et al., Detection of Minimal Residual Cells Carrying the t(14;18) by DNA Sequence Amplification, Science, vol. 237, Jul. 1987.

Saiki et al., Primer-Directed Enzymatic Amplification of DNA with a Thermostable DNA Polymerase, Science, vol. 239, Jan. 1988, pp. 487–491.

Stoflet et al., Genomic Amplification with Transcript Sequencing, Science, vol. 239, Jan. 1988, pp. 491–494.

Mullis et al., Specific Enzymatic Amplification of DNA in Vitro: The Polymerase Chain Reaction, Cold Spring Harbor Symposia on Quantitative Biology, vol. LI, 1986, pp. 263–273.

Scharf et al., Direct Cloning and Sequence Analysis of Enzymatically Amplified Genomic Sequences, Science, vol. 233, Sep. 1986, pp. 1076–1078.

Bialy et al., Amplified Genes and Frame-Shift Mutations, Bio/Technology, vol. 5, Dec. 1987, pp. 1268.

Wrischnik et al., Length Mutations in Human Mitochondrial DNA: Direct Sequencing of Enzymatically Amplified DNA, Nucleic Acids Research, vol. 15, No. 2, 1987, pp. 529–543.

Impraim et al., Analysis of DNA Extracted from Formalin-Fixed, Paraffin-Embedded Tissues by Enzymatic Amplification and Hybridization with Sequence-Specific Oligonucleotides, Biochemical and Biophysical Research Communications, vol. 142, No. 3, 1987, pp. 710–716.

Rollo et al., Polymerase Chain Reaction Fingerprints, Nucleic Acids Research, vol. 15, No. 21, 1987, pp. 9094.

Saiki et al., Analysis of Enzymatically Amplified B--Globin and HLA-DQa DNA with Allele-Specific Oligonucleotide Probes, Nature, vol. 324, Nov. 13, 1986, pp. 163–166.

Lee et al., The Gene Located at Chromosome 18 Band q21 is Rearranged in Uncultured Diffuse Lymphomas as Well as Follicular Lymphomas, Blood, vol. 70, No. 1, Jul. 1987, pp. 90–95.

Weiss et al., Molecular Analysis of the t(14;18) Chromosomal Translocation in Malignant Lymphomas, The New England Journal of Medicine, vol. 317, No. 19, Nov. 5, 1987, pp. 1185–1189.

Tsukimoto et al., The t(14;18) Chromosome Translocations Involved in B-Cell Neoplasms Result from Mistakes in VDJ Joining, Science, vol. 229, Sep. 1985, pp. 1390–1393.

Ravetch et al., Structure of the Human Immunoglobulin u Locus: Characterization of Embryonic and Rearranged J and D Genes, Cell, vol. 27, Dec. 1981, pp. 583–591.

Tsujimoto et al., Analysis of the Structure, Transcripts, and Protein Products of bel-2, The Gene Involved in Human Follicular Lymphoma, Proc. Natl. Acad. Sci., USA 83 (1986), pp. 5214–5218.

Cleary et al., Cloning and Structural Analysis of cDNAs for bcl-2 and a Hybrid bcl-2/Immunoglobulin Transcript Resulting from the t(14;18) Translocation, Cell, vol. 47, Oct. 10, 1986, pp. 19–28.

Bakhshi et al., Mechanism of the t(14;18) Chromosomal Translocation: Structural Analysis of Both Derivative 14 and 18 Reciprocal Partners, Proc. Natl. Acad. Sci. USA, vol. 84, Apr. 1987, pp. 2396–2400.

Whang-Peng et al., Clinical Implications of Cytogenetic Variants in Chronic Myelocytic Leukemia (CML), Blood, vol. 32, No. 5, Nov. 1968, pp. 755–766.

Groffen et al., Philadelphia Chromosomal Breakpoints are Clustered within a Limited Region, bcr, on Chromosome 22, Cell, vol. 36, Jan. 1984, pp. 93–99.

Heisterkamp et al., Structural Organization of the bcr Gene and its Role in the Ph' Translocation, Nature, vol. 315, Jun. 1985, pp. 758–761.

Heisterkamp et al., Localization of the c-abl Oncogene Adjacent to a Translocation Break Point in Chronic Myelocytic Leukaemia, Nature, vol. 306, Nov. 17, 1983, pp. 239–242.

Shtivelman et al., Alternative Splicing of RNAs Transcribed from the Human abl Gene and from the bcr-abl Fused Gene, Cell, vol. 47, Oct. 24, 1986, pp. 277–284.

Shtivelman et al., ber-abl RNA in Patients with Chronic Myelogenous Leukemia, Blood, vol. 69, Mar. 1987, pp. 971–973.

Berk et al., Sizing and Mapping of Early Adenovirus mRNAs by Gel Electrophoresis of S1 Endonuclease-Digested Hybrids, Cell, vol. 12, Nov. 1977, pp. 721–732.

Ando, A Nuclease Specific for Heat-Denatured DNA Isolated from A Product of Aspergillus Oryzae, Biochimica Et Biophysica Acta, 114, 1966, pp. 158–168.

Tsujimoto et al., Involvement of the bcl-2 Gene in Human Follicular Lymphoma, Science, vol. 228, Jun. 21, 1985, pp. 1440–1443.

(List continued on next page.)

OTHER PUBLICATIONS

Fukuhara et al., Chromosome Abnormalities in Poorly Differentiated Lymphocytic Lymphoma, Cancer Research, vol. 39, Aug. 1979, pp. 3119-3128.

Yunis et al., Distinctive Chromosomal Abnormalities in Histologic Subtypes of Non-Hodgkin's Lymphoma, The New England Journal of Medicine, vol. 307, No. 20, Nov. 11, 1982, pp. 1231-1236.

Bloomfield et al., Nonrandom Abnormalities in Lymphoma, Cancer Research, vol. 43, Jun. 1983, pp. 2975-2984.

Tsujimoto et al., Cloning of the Chromosome Breakpoint of Neoplastic B Cells with the t(14;18) Chromosome Translocation, Science, vol. 226, Nov. 30, 1984, pp. 1097-1099.

Bakshi et al., Cloning the Chromosomal Breakpoint of t(14;18) Human Lymphomas: Clustering Around $J_H$ on Chromosome 14 and Near a Transcriptional Unit on 18, Cell, vol. 41, Jul 1985, pp. 899-906.

Cleary et al., Nucleotide Sequence of a t(14;18) Chromosomal Breakpoint in Follicular Lymphoma and Demonstration of a Breakpoint-Cluster Region Near a Transcriptionally Active Locus on Chromosome 18, Proc. Natl. Acad. Sci, USA, vol. 82, Nov. 1985, pp. 7439-7443.

Saiki et al., Enzymatic Amplification of B-Globin Genomic Sequences and Restriction Site Analysis for Diagnosis of Sickle Cell Anemia, Science, vol. 230, Dec. 20, 1985, pp. 1350-1354.

Smith et al., Ciculating Monoclonal B Lymphocytes in Non-Hodgkin's Lymphoma, The New England Journal of Medicine, vol. 311, No. 23, Dec. 6, 1984, pp. 1476-1481.

Kozma et al., "The Human c-Kirsten Ras Gene Is Activated By a Novel Mutation In Codon 13 In the Breast Carcinoma Cell Line MDA-MB231," Nucleic Acids Research, vol. 15, No. 15, 1987, pp. 5963-5971.

1 2 3 4 5 6    1 2 3 4 5 6 7 8    1 2 3 4 5 6 7 8
*Fig. 3A*    *Fig. 3B*    *Fig. 3C*

5,024,934

DETECTION OF MINIMAL NUMBERS OF NEOPLASTIC CELLS CARRYING DNA TRANSLOCATIONS BY DNA SEQUENCE AMPLIFICATION

BACKGROUND OF THE INVENTION

Frequency of recurrence is one of the major problems in cancer treatment Relapse from clinically undetectable residual disease is the most likely mechanism. Detection of minimal disease is extremely difficult since tumor specific markers are not readily available. Molecular technology has provided a means to demonstrate residual disease by identifying clonal rearrangement patterns that are present in malignant hematopoietic cells (1). Southern blot hybridization detects neoplastic cells at levels as low as 1% of the total number of cells (2). However, one of the major drawbacks in this situation is that it is difficult to be certain that faint nongermline bands indeed represent clonal rearrangements Furthermore, no rearranged bands can be detected in cases in which the concentration of neoplastic cells is below 1%. Theoretically this occurs frequently while patients are in remission.

The karyotypic abnormality, t(14;18)(q32;q21), has been observed in approximately 90% of human follicular lymphomas (3-5). This translocation frequently results in rearrangement of a putative oncogene "bc1-2" which resides at chromosome 18 band q21 (6). In the majority of cases with the t(14;18), the molecular breakpoints on chromosome 18q21 cluster within a 4.3 kilobase (kb) Hind III restriction fragment or more specifically a 2.8 kb EcoR1-Hind III restriction fragment which has recently been designated the t(14;18) major breakpoint cluster region (mbr) (7-11). DNA sequencing of the crossover sites revealed that breakpoints on chromosome 18q21 were clustered within 150 base pairs (bp) of each other and breakpoints on chromosome 14 were located close to the 5' end of one of the joining (J) segments (J1 to J6) of the immunoglobulin heavy chain locus (JH) (11-13).

Saiki et al. have recently utilized a new technique, sequence amplification by polymerase chain reaction (PCR), to diagnose sickle cell anemia prenatally (14). This technique is mainly applicable to genetic disorders with a point DNA mutation. It is difficult to apply PCR to the detection of chromosomal translocation because of the variability of molecular breakpoints on chromosomes. The present invention describes a method of utilizing the PCR technique to amplify DNA sequences flanking the crossover site of a chromosomal translocation such as t(14;18) which is characteristic of a tumor. Since cells carrying the subject t(4;18) translocation are unique to malignant hematopoietic cells, detection and amplification of such sequences can be used as evidence for minimal residual disease. The present invention also demonstrates the unique consequence of applying the PCR technique to a chromosomal translocation, i.e., preferential amplification of the hybrid DNA sequences of the chromosomal translocation, but not the normal DNA sequence.

SUMMARY OF THE INVENTION

The present invention involves a method for detecting minimal numbers of neoplastic cells in an individual. These neoplastic cells are typically residual cells from a lymphoma incompletely eradicated by antitumor therapy. The subject neoplastic cells of the present invention may be characterized by a DNA translocation related to a specific chromosomal breakpoint clustering region. A neoplasm to which the present invention may be applied is most typically a human follicular lymphoma although it may also be characterized as a non-Hodgkin's lymphoma, a pre-B-cell or B-cell leukemia, a B-cell lymphoma, a large cell lymphoma, a diffuse large cell lymphoma or a small noncleaved cell lymphoma.

The method of the present invention typically includes the following steps.

(1) Incubating a mixture comprising:
 (a) deoxyribonucleotide triphosphates including deoxyadenosine triphosphate, deoxythymidine triphosphate, deoxycytosine triphosphate and deoxyguanosine triphosphate;
 (b) DNA from cells, most particularly lymphoid cells from blood, bone marrow or lymph node of the individual;
 (c) DNA polymerase, preferably the Klenow fragment of *E. coli* DNA polymerase or *Thermus aquaticus* DNA polymerase.
 (d) a first oligonucleotide primer, said first primer being identical to an upstream nucleotide sequence flanking the coding DNA translocation, derived from one chromosome such as chromosome 18q21.
 (e) a second oligonucleotide primer, said second primer being complementary to a downstream nucleotide sequence flanking the coding DNA translocation derived from the other chromosome, such as chromosome 14q32. (The primers are present in the incubation mixture in excess of that needed to bind complementary oligonucleotide sequences of the DNA and are preferably at about a 1 micromolar (uM) concentration.).

The incubating is under conditions allowing annealing of the primers to the crossover site of the chromosomal translocation DNA sequences and a substantial portion of flanking DNA sequences.

(2) The incubating is then terminated by DNA denaturation. The cycles of annealing, synthesis and denaturation are repeated numerous times (preferably 20-50) to facilitate duplications of the original and previously synthesized translocated and substantial flanking DNA sequences. The repetition is carried out in a manner allowing exponential amplification of DNA sequences extending from primers and including a DNA region complementary to the other oligonucleotide primers. This amplification is an extension of each primer to and including a post-translocational DNA sequence complementary to the other member of the primer set being used.

(3) The exponentially amplified DNA is probed for the presence of oligonucleotide sequences characterizing the translocation region. Elongation of each primer in this system eventually involves the addition thereto of a coding or non-coding translocation DNA sequence usually terminating in the oligonucleotide complementary to the other member of the primer set being utilized. Positive probings indicate the presence of neoplastic cells in the sample of the individual's cells, since DNA characterizing said neoplastic cells was specifically amplified and probed.

The above-described procedure may likewise be directed to detection of neoplastic cells characterized by DNA translocation related to more than one specific breakpoint clustering regions. The method described above could be modified as follows where more than one breakpoint clustering region may be being amplified and probed. The incubated mixture could have at least two sets of oligonucleotide primers, each set flanking a particular breakpoint clustering region. Each set of oligonucleotide primers consists of a first oligonucleotide primer and a second oligonucleotide primer, said first oligonucleotide primer being identical to an upstream coding nucleotide sequence flanking a particular DNA breakpoint clustering region of a chromosomal translocation and said second primer being complementary to a downstream coding nucleotide sequence flanking the same particular DNA breakpoint clustering region of this translocation. The mixture of primers, DNA from cells, deoxynucleotide triphosphates and DNA polymerase and the incubating is again under conditions facilitating annealing of the primers to the crossover sites of the translocations and synthesis of the sequences of coding and non-coding translocation DNA and including a substantial portion of flanking DNA, such a substantial portion including a DNA portion complementary to the other member of the particular primer set being used. Again the incubating is terminated by DNA denaturations. The annealing, synthesis and denaturation are repeated in a cyclic manner to facilitate further synthesis of the original DNA and of newly synthesized DNA, said repeating being carried out in a manner allowing exponential amplification of DNA sequences between initiating oligonucleotide primers and sequences complementary to the other member of the primer set. Lastly, the exponentially amplified DNA is probed for the presence of oligonucleotide sequences characterizing the translocation of DNA sequence. The presence of neoplastic cells in the sample of the individual's cells is identified by positive probings. Such probings are most typically carried out by Southern blot or Dot blot procedures whose methodologies are well-known to those skilled in the relevant arts. The method of the present invention involves in vitro synthesis of the DNA sequences at the crossover site of a tumor characteristic chromosomal translocation by primer extension and a substantial flanking DNA region including that nucleotide sequence complementary to the primers.

The oligonucleotide primers utilized in the methods of the present invention are preferably complementary or identical to DNA sequences located within about 1000 bases of the nearest chromosomal breakpoint clustering region. These oligonucleotide primers are further preferably between about 12 and about 20 nucleotides in length.

The method of the present invention most particularly involves detection of neoplasia such as those having the t(14;18) translocation. These neoplasia characteristically have a major breakpoint clustering region in the majority of cases and a minor breakpoint clustering region in the minority of the cases, the major breakpoint clustering region being the mbr region and minor breakpoint clustering region being the mcr region. In cases where two breakpoint regions are to be analyzed, two sets of oligonucleotide primers are added to the above described incubation mixture and the probings are derived from the crossover sites of the translocated DNA.

The probing step of the present invention, as mentioned above, typically involves Southern blot analysis or Dot blot analysis. Such Southern blot analysis characteristically includes gel electrophoresis of the PCR amplified DNA segments, transfer of electrophoresed fragments to a nitrocellulose filter or nylon filter and probing the filter of nucleotide sequences binding the probes of interest. Dot blot analysis is similar to the above procedure except that the PCR-amplified DNA is denatured in situ and then blotted to the filter without gel electrophoresis.

The method of the present invention preferably involves the detection of minimal numbers of neoplastic cells with a chromosomal translocation. Such neoplastic cells, particularly those characterized by a t(14;18) chromosomal translocation are most frequently human follicular lymphomas. Preferred subject neoplasia of the present invention may also be characterized as being a non-Hodgkin's lymphoma, B-cell or pre-B cell leukemia, B-cell lymphoma, large cell lymphoma, diffuse large cell lymphoma or small noncleaved cell lymphoma.

BRIEF DESCRIPTION OF THE DRAWINGS

FIG. 3 shows a Southern blot analysis of PCR-amplified genomic DNA with radioactively labeled primer 18q21(+) and primer $J_H(-)$.

DESCRIPTION OF THE PREFERRED EMBODIMENT

Figure 1:
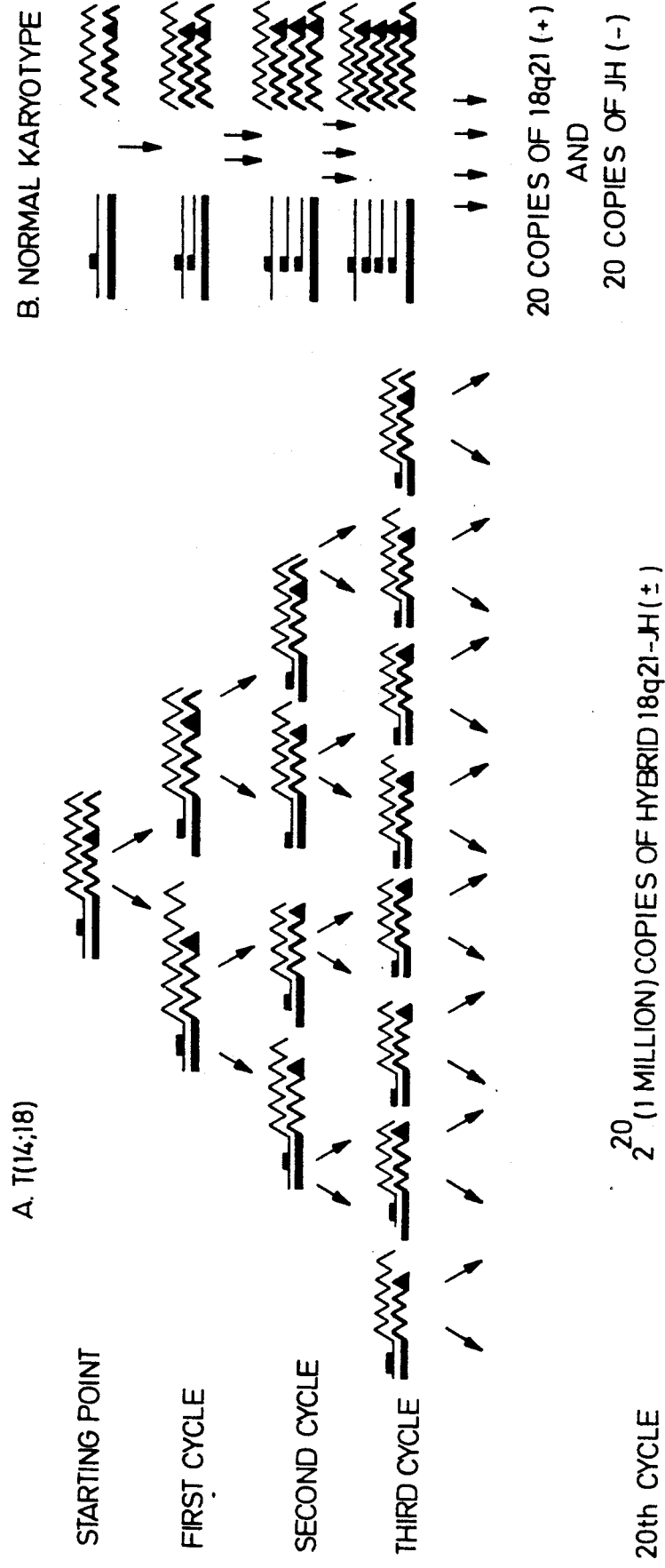
FIG. 1 schematically illustrates preferential PCR amplification of the hybrid 18q21-JH DNA sequence.

The present invention involves using the polymerase chain reaction (PCR) technique to amplify DNA sequences that flank the crossover site of a chromosomal translocation characteristic for follicular lymphomas, t(14;18)(q32;q21). This technique permitted the detection of cells carrying the t(14;18) hybrid DNA sequences at a dilution of 1:100,000. The remission marrow and blood samples of patients with follicular lymphoma and the t(14;18) fail to show any abnormality by morphological examination and conventional Southern blot analysis. However, the t(14;18) hybrid DNA sequences were detected by the PCR technique. Thus, the present invention described a highly sensitive tool to detect minimal residual cells carrying the t(14;18) and has the potential to identify a subpopulation of patients with subclinical disease. This invention can also be used for the early detection and rapid diagnosis of a neoplasm with the t(14;18) as well as for the diagnosis of the t(14;18) by using a small amount of DNA sample (at the level of several nanograms (ng)).

Polymerase chain reaction (PCR) is a technique which allows exponential amplification of the target DNA sequences. It has been used for rapid diagnosis of certain hereditary genetic disorders in which a point DNA mutation is present and each individual cell contains the same abnormality. The present invention involves the first application of PCR to a chromosomal translocation, thus, resulting in preferential amplification of tumor specific hybrid DNA sequences in a minimal number of cells carrying a chromosomal translocation among several hundred thousand normal cells.

Two synthetic oligonucleotides were prepared as primers for PCR usage. These two primers were expected to flank the crossover site of the t(14;18) in the majority of cases. Primer 18q21(+), 5'-TTTGACCTT-TAG-3', was identical to the sequences of the (+)-strand of chromosome 18q21 (11-13) and primer $J_H(-)$, 3'-CAGAGGAGTCCA-5', was complementary to the sequences present in the 3' end of each (+)-strand J segment (15). Therefore, this primer always flanks the breakpoint on the $J_H$ region even though the breakpoint varies from J1 to J6 from case to case. In case of the t(14;18), copies of the (+)-strand hybrid 18q21-$J_H$ DNA sequences were synthesized from primer 18q21(+) and copies of the (-)-strand hybrid 18q21-$J_H$ DNA sequences were synthesized from primer $J_H(-)$. New copies of the (+)-strand and the (-)-strand hybrid 18q21-$J_H$ DNA sequences in turn became templates of primer $J_H(-)$ and primer 18q21(+) respectively. Therefore, DNA sequences flanking the crossover site of the t(14;18) were amplified exponentially as PCR was carried out (FIG. 1A). In contrast, such amplification could not be generated in cases without the t(14;18) because no new templates for the primers could be synthesized (FIG. 1B). These two primers could also be used as probes to detect newly synthesized hybrid 18q21-$J_H$ DNA sequences, which were generated in case of the t(14;18), but not the new copies of 18q21(+) or $J_H(-)$ DNA sequences which were synthesized in cases without the t(14;18). Another oligonucleotide 18q21(+)II, 5'-CACAGACCCACC-CAGAGCCC-3', deduced from the mbr region [27 bases 3' to the primer 18q21(+)], was used as an "internal" probe to further confirm that the PCR amplified DNA segments contained the hybrid 18q21-$J_H$ sequences (11-13). Since 18q21(+)II derived from sequences of the (+)-strand chromosome 18q21, it cannot hybridize with sequences extended from primer 18q21(+). In contrast, it will hybridize with sequences extended from primer $J_H(-)$ in case of the t(14;18). Therefore, signals detected by the radiolabeled 18q21(+)II probe strongly indicate presence of the hybrid 18q21-$J_H$ sequences.

FIG. 1 schematically illustrates the mechanism by which PCR preferentially amplifies the hybrid 18q21-JH DNA sequences, but not the normal DNA sequences. As shown in FIG. 1(A), in cases of the t(14;18), the hybrid 18q21-$J_H$(+) and 18q21(+)-JH(-) DNA sequences were synthesized from primer 18q21(+) and primer JH(-) respectively. The primers are also complementary to the newly synthesized hybrid 18q21-JH(±) DNA sequences which, in turn, become templates for the primers. Therefore, exponential amplification of the hybrid 18q21-JH(±) DNA sequences are generated, i.e., $Y=(1+E)^N$ where Y is the extent of yield, E is the mean efficiency per PCR cycle and N is the number of PCR cycles carried out. Presuming E=100% and N=20, the final yield is $2^{20}$ copies of hybrid 18q21-JH(+) DNA sequences.

As shown in FIG. 1(B), in case of normal karyotype, the newly synthesized 18q21(+) and JH(-) DNA sequences can not be templates for the primers. Therefore, the final yield was calculated as the following formula: $y=2n \times e$, where y is the extent of yield, n is the number of PCR cycles and e is the mean efficiency per cycle.

By means of DNA sequencing, about 60% of follicular lymphomas have been shown to have breakpoints on chromosome 18q21 tightly clustered within 150 base pairs of each other, which is named the molecular breakpoint hot spot (11-13). Our primer 18q21(+) was derived from the (+)-strand DNA sequence of chromosome 18q21 immediately 5' to the molecular breakpoint hot spot. One "internal" probe, 18q21(+)II, was derived from the (+)-strand 18q21 DNA sequence 27 bases 3' to primer 18q21(+). The breakpoint on chromosome 14q32 is also very consistent from case to case. It always occurs at the 5' end of one of the J-segments (J1-J6) of the immunoglobulin heavy chain gene. Since the sequences at the 3' end of each J-segment are the same (15), primer $J_H(-)$ with sequence derived from this region was made. Therefore, Primer $J_H(-)$ would always anneal to the crossover site of the t(14;18) even though the breakpoints on chromosome 14q32 vary from J1 to J6 from case to case.

In order to establish the use of PCR to amplify the DNA sequences flanking the crossover sites of the t(14;18), three representative DNA samples were selected. Sample A was from a lymph node of follicular lymphoma with the t(14;18) breakpoint occurring within the mbr region. Sample B was from a lymph node of reactive lymphadenitis with normal karyotype Sample C as from a lymph node of follicular lymphoma with the t(14;18) breakpoint 3' to the mbr region. These samples were analyzed by Southern blot hybridization with a human genomic DNA fragment specific for the mbr region of chromosome 18q21 (FIG. 2A) (7,11). As shown in FIG. 2B, Lanes 1 and 4, two rearranged bands were detected in Sample A, indicating the breakpoint on chromosome 18q21 occurring within mbr. In Sample C only one rearranged band was detected by restriction endonuclease Sst1 and no rearrangement was detected with HindIII (FIG. 2B, Lanes 3 and 6). Therefore, the breakpoint occurred 3' to mbr (within the Hind III-Sst1 restriction fragment).

Figure 2A:
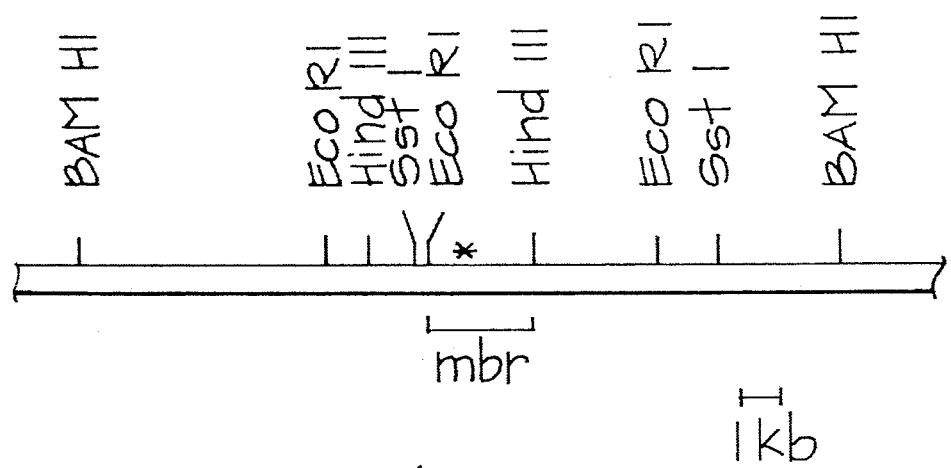
FIG. 2(A) shows a partial restriction enzyme map surrounding the mbr region of chromosome 18 band q21.
Figure 2B:
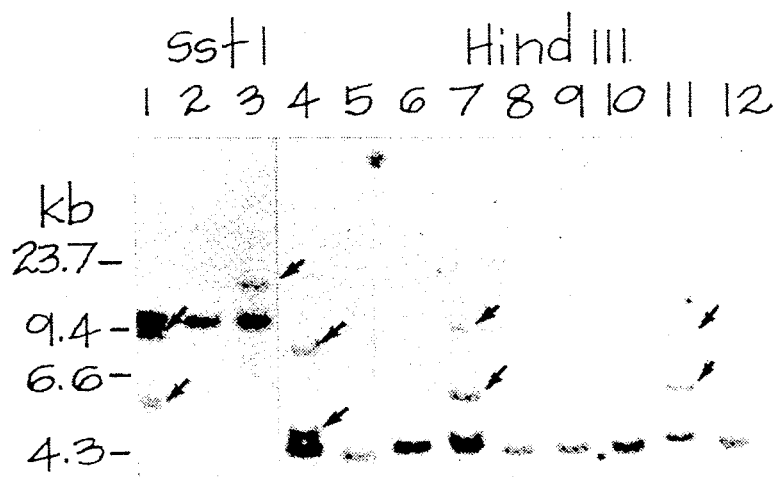
FIG. 2(B) shows Southern blot hybridization with labeled mbr probe of restriction enzyme digested DNA samples.

FIG. 2(A) shows a partial restriction enzyme map surrounding the mbr region of chromosome 18 band q21. The solid bar represents the germline DNA structure of chromosome 18 band q21 (7). The horizontal line labeled as mbr indicates the t(14;18) major breakpoint cluster region and the probe used for Southern blot hybridization to map the chromosomal breakpoints of the t(14;18) on chromosome 18q21. The asterisk (*) indicates the t(14;18) breakpoint hot spot where primer 18q21(+) was deduced (1,13). (B) Southern blot hybridization with mbr probe. DNA's were digested with enzyme Sst1 or enzyme HindIII and size fractionated on a 0.8% agarose gel, transferred to a nylon filter, and hybridized with a radiolabeled mbr probe. The rearranged bands are indicated by arrows. Lanes 1-3 were Sst1 digested Sample A, B and C respectively. Lanes 4-6 were HindIII digested Sample A, B and C respectively. Lanes 7-10 were DNA samples obtained from Patient 1 and were digested with enzyme HindIII (Lane 7: pretreatment bone marrow sample obtained in October of 1985; Lane 8: remission blood sample obtained in June of 1986; Lane 9: remission marrow sample obtained in June of 1986); Lane 10: remission marrow sample obtained in September of 1986). Lane 11 and 12 were DNA samples obtained from Patient 2 and were digested with HindIII. (Lane 11: pretreatment lymph node sample obtained in January of 1986; Lane 12: remission marrow sample obtained in October of 1986).

Figure 4:
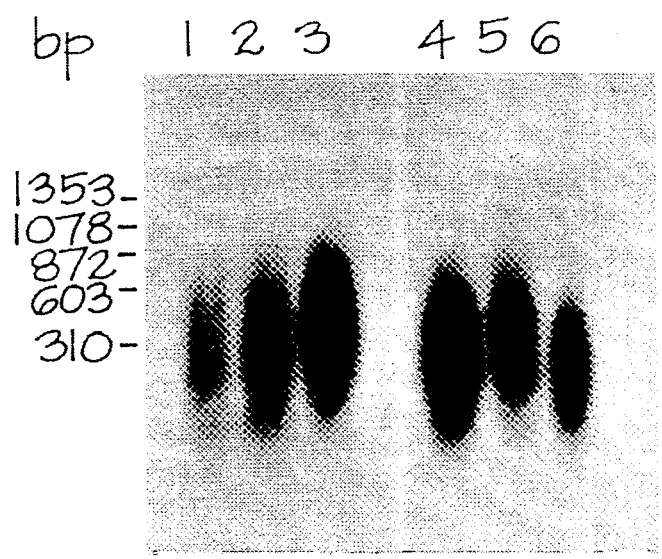
FIG. 4 shows a Southern blot analysis of PCR-amplified genomic DNA with radioactively labeled oligonucleotide 18q21(+)II.

These rearranged bands in Sample A and C also comigrated with the immunoglobulin JH gene, which confirmed that breakpoint on chromosome 14 relocated in the $J_H$ region. These three samples were subjected to PCR. The hybrid 18q21-$J_H$ DNA sequences in Sample A were amplified and the signals were detected after the 15th cycle by radiolabeled primers 18q21 and $J_H$ (FIG. 3A). The amplified DNA segments also hybridized with radiolabeled 18q21(+)II, which further confirmed presence of the hybrid 18q21-J$_H$ sequences (FIG. 4, Lanes 1-3). Sample B was not amplifiable because there were no hybrid 18q21-J$_H$ DNA sequences present. Sample C could not be amplified because primer 18q21(+) was too far upstream (>1kb) from the breakpoint. Since approximately 60% of follicular lymphoma samples were mapped to have the t(14;18) breakpoint occurring within the mbr region (8,10), it was estimated that close to 60% of follicular lymphomas will be amplifiable by the above described specific PCR technique.

Another manipulation was performed to show that the PCR-related method of the present invention could preferentially amplify the hybrid 18q21-J$_H$ DNA sequences, but not the normal DNA sequences. Dilutions of Sample A and Sample B in different ratios, 1:100, 1:5,000, and 1:100,000, were subjected to PCR. In the first two instances, the hybrid 18q21-J$_H$ DNA sequences were amplified and signals were detected after the 20th cycle of PCR as shown in FIG. 3B and FIG. 4, Lane 4. In the last instance (1:100,000 dilution), a strong and convincing signal was detected at the 30th cycle by using a mixture of radiolabeled primers 18q21(+) and J$_H$(−) as a probe (FIG. 3C, Lane 3). The presence of the hybrid 18q21-J$_H$ sequence was also further confirmed by the radiolabeled "internal" probe 18q21(+)II.

FIG. 3 shows a Southern blot analysis of PCR amplified genomic DNA with radiolabeled primer 18q21(+) and primer J$_H$(−). Samples (1ug) of genomic DNA were dispensed in microcentrifuge tubes then denatured at 100° C. for 5 minutes, centrifuged for 10 seconds to remove the condensation, and adjusted to 100 ul in a buffer containing 10 mM tris, pH 7.5, 50 mM NaCl, 10 mM MgCl$_2$ 1.5 mM deOxynucleotide triphosphate (each of 4 was used), 1 uM primer 18q21(+) and 1 uM primer J$_H$(−). The samples were then transferred to a 42° C. heat block for 2 minutes to allow annealing, followed by adding 1 ul of the Klenow fragment of E. coli DNA polymerase I (1 unit/ul) and 1 ul of 0.1 M dithiothreitol (DTT) and allowing extension of DNA sequences for 5 minutes. The cycle—denaturation, reannealing and extension—was repeated for 19 to 29 more times as needed, except that subsequent denaturations were performed at 95° C. for 2 minutes. Amplified DNA (amplimers) from the PCR equivalent to 25 nanograms (ng) of the original DNA's was loaded on a 2% alkaline agarose minigel, fractionated by electrophoresis (50V) for 2 hours, and then neutralized and transferred to a nylon filter. Prehybridization, hybridization and washing of filters were carried out as described by Saiki et al. (14). A mixture of primer 18q21(+) and J$_H$(−) was radiolabeled with [gamma-$^{32}$P]ATP to a specific radioactivity of >3uCi/pmol (microcurie/picomole) oligonucleotide and used as a probe. Autoradiography was carried out with a single intensification screen at −70° C. for 48 hours. (A) 1 microgram (ug) of HindIII-digested Sample A (Lane 1) was compared with 25 ng of PCR amplified Sample A at various time points: the third cycle (Lane 2), the 7th cycle (Lane 3), the 10th cycle (Lane 4), the 15th cycle (Lane 5) and the 20th cycle (Lane 6). (B) Dilutions of Sample A and Sample B in different ratios (1:100 and 1:5,000) were subjected to PCR and 25 ng of PCR amplified DNA's were collected at various time points: Lanes 1-4 represent mixtures of 1:100 dilution amplified for 10, 15, 20 and 24 cycles respectively; Lanes 5-8 represent mixture of 1:5,000 dilution amplified for 15, 20, 25, 30 cycles respectively. (C) Lane 1: Sample B subjected to PCR for 30 cycles; Lanes 2 and 3: Mixture of Samples A and B in 1:100,000 ratio amplified for 20 and 20 cycles of PCR respectively; Lanes 4-6: remission marrow and blood samples were obtained from Patient 1 and subjected to PCR for 27 cycles, corresponding to samples shown in FIG. 2, Lanes 8-10 respectively; Lane 7: pretreatment tumor sample obtained from Patient 2 and amplified for 20 cycles of PCR: Lane 8: remission marrow sample obtained from Patient 2 and subjected to PCR for 27 cycles. The φX174 HaeIII molecular weight markers are labeled on the left of each autoradiograph.

FIG. 4 shows a Southern blot analysis of PCR amplified genomic DNA with radiolabeled oligonucleotide 18q21(+)II. The PCR, radiolabeling, hybridization condition washing condition and autoradiography were carried out as described above except that the radiolabeled oligonucleotide 18q21(+)II with specific activity of >3uCi/pmol was used as a probe and autoradiography was carried out for 20 hours. Lanes 1, 2 and 3: 25 ng of Sample A's were amplified for 20, 25 and 30 cycles respectively. Lane 4: 25 ng of mixture of Sample A and Sample B in 1:5,000 dilution were subjected to PCR for 40 cycles. Lane 5 and 6: 25 ng of remission marrow samples obtained from Patient 1 in June and September of 1986 respectively were amplified for 40 cycles. The φx174 HaeIII molecular weight markers are labeled on the left of the autoradiograph shown in FIG. 4.

Sequential follow-up studies in two patients with follicular lymphoma and the t(14;18) translocation were performed. The pretreatment tumor samples were shown to have chromosomal breakpoints occurring within mbr (FIG. 2B, Lanes 7 and 11). The remission marrow and blood samples obtained from these two patients were first analyzed by morphological examination and conventional Southern blot hybridization with a radiolabeled mbr probe. All the samples appeared normal since none of them demonstrated any morphologic abnormality or rearranged bands (FIG. 2B, Lanes 8-10 and 12). However, hybrid DNA sequences were markedly amplified and thus clearly detected by the PCR technique in samples obtained from Patient 1 (FIG. 3C, Lanes 4-6 and FIG. 4, Lanes 5 and 6) indicating the presence of residual neoplastic cells carrying the t(14;18). Even though the hybrid 18q21-J$_H$ DNA sequences were amplifiable in the pretreatment tumor sample obtained from Patient 2 (FIG. 3C, Lane 7), no hybrid DNA sequences were detected in the remission marrow sample by the PCR technique (FIG. 3C, Lane 8). These findings indicated that the concentration of neoplastic cells carrying the t(14;18) was too low to be detected by our current techniques or the patient was completely free of tumor and there was no t(14;18) target DNA sequences present for amplification.

In addition to the major breakpoint clustering region (mbr) observed in about 60% of follicular lymphoma, a new breakpoint clustering region (mcr) in the t(14;18) translocation has recently been described in about 30% of follicular lymphomas (16). Using proper primers derived from this region, the technique of the present invention may be applied to samples with the t(14;18) breakpoint occurring within this region. Furthermore, the t(14;18) has also been observed in about 20-40% of diffuse large cell lymphoma and 20% of small noncleaved cell lymphoma (9,16). Therefore, this technique can also be applied to subtypes of malignant lymphomas with the t(14;18) translocation besides follicular lymphoma. Finally, this technique can be applied to any chromosomal translocation if the breakpoints on both chromosomes are limited to a small DNA segment (about one kilobase), such as the t(11;14) translocation.

Utilizing the PCR technique of the present invention in a preferred application, a fundamental and very important question was addressed, i.e., were there small numbers of circulating cells carrying the t(14;18) in patients with follicular lymphoma in early clinical stages of disease and in clinical remission?

Ten blood samples from patients with follicular lymphoma and the t(14;18) breakpoint within the mbr region were initially selected. These samples were obtained in various clinical states: 3, before treatment, 2, at partial remission and 5, at complete remission. Morphologically these samples appeared normal. They were analyzed both by the PCR assay and Southern blot analysis (Table I).

TABLE I
DETECTION OF LYMPHOMA IN PERIPHERAL BLOOD BY THE PCR TECHNIQUE CORRELATION WITH SOUTHERN BLOT ANALYSIS ACCORDING TO CLINICAL STATUS

| CLINICAL STATUS | PATIENTS STUDIED | POSITIVE BY PCR | POSITIVE BY SOUTHERN |
|---|---|---|---|
| BEFORE TREATMENT | 3 | 3 | 1 |
| PARTIAL REMISSION | 2 | 2 | 0 |
| COMPLETE REMISSION | 5 | 4 | 1 |
| TOTAL | 10 | 9 | 2 |

Among the 10 samples analyzed, 9 were positive for the translocation by the PCR assay. In contrast, clonal bcl-2 gene rearrangement could be detected in only 2 cases by traditional Southern blot analysis. Three out of 3 samples obtained before treatment and 2 out of 2 samples obtained at partial remission were positive by the PCR assay. These findings indicated that when there was clinically detectable disease, there were small numbers of cells carrying the t(14;18) in circulation. The most intriguing finding was that even when patients achieved complete remission, circulating cells carrying the t(14;18) were detected in 4 out of 5 instances by the PCR assay.

The technique of the present invention was also used to determine whether there were circulating cells with the t(14;18) in an early clinical stage of the disease. As shown in Table II, three pretreatment blood samples from 3 patients whose lymph nodes were known to have the t(14;18) breakpoint within the mbr region were analyzed.

TABLE II
DETECTION OF LYMPHOMA IN PERIPHERAL BLOOD BY THE PCR TECHNIQUE CORRELATION WITH ANN ARBOR STAGE BEFORE THERAPY

| ANN ARBOR STAGE | BREAKPOINT WITHIN mbr | | BREAKPOINT NOT STUDIED | |
|---|---|---|---|---|
| | PATIENTS STUDIED | PATIENTS POSITIVE | PATIENTS STUDIED | PATIENTS POSITIVE |
| I | 0 | 0 | 2 | 1 |
| II | 1 | 1 | 4 | 3 |
| III | 0 | 0 | 3 | 3 |
| IV | 2 | 2 | 1 | 1 |
| TOTAL | 3 | 3 | 10 | 8 |

All three of these samples were positive by the present PCR assay. In correlation with the clinical stage, one was from stage II disease and the other 2 were from stage IV disease. Ten pretreatment blood samples were analyzed from 10 patients for whom no DNA samples from the lymph nodes were available to study. Since about 60% of follicular lymphomas have the breakpoint within the mbr region, it was expected that approximately 60% of blood samples should be amplifiable if involving a lymphoma. As shown in Table II, 8 out of these 10 samples were positive. Even in the 6 samples obtained from clinical stage I or stage II disease, 4 were positive. The reason for the remaining being negative was most likely due to absence of a breakpoint within the mbr region. These findings strongly indicated that follicular lymphoma was a systemic disease despite the fact that the disease might be localized clinically.

To study the mechanism of frequent recurrences observed in follicular lymphoma, blood samples obtained from patients in clinical remission at various time points of the remission were analyzed by the PCR assay. As shown in Table III, five samples were obtained from patients at the time of remission of less than one year and who were known to have a breakpoint within the mbr region.

TABLE III
DETECTION OF LYMPHOMA IN PERIPHERAL BLOOD BY THE PCR TECHNIQUE IN COMPLETE RESPONDERS CORRELATION WITH DURATION OF COMPLETE REMISSION

| STUDIED YEARS IN CONTINUOUS REMISSION | BREAKPOINT WITHIN MBR | | BREAKPOINT NOT | |
|---|---|---|---|---|
| | PATIENTS STUDIED | PATIENTS POSITIVE | PATIENTS STUDIED | PATIENTS POSITIVE |
| >1 YEAR | 5 | 4 | 1 | 1 |
| 2-3 YEARS | 0 | 0 | 3 | 2 |
| TOTAL | 5 | 4 | 4 | 3 |

Four of these 5 patients showed evidence of subclinical disease by the PCR assay. Similarly in the 4 cases in whom the breakpoint was not studied, 3 were positive. In these 3 instances, 2 had been in remission for more than 2 years. These findings suggested that continuous relapse of follicular lymphoma may be due to recurrence of minimal residual disease which progresses slowly.

It may be that the PCR assay can reliably predict the likelihood of future relapse patients in remission. There were 5 complete responders in remission who had been followed clinically for more than 8 months after the results of the PCR assay were available. As shown in Table IV, in the 4 patients whose remission blood samples were positive, 3 have relapsed: 2 relapsed clinically and 1 developed clonal bcl-2 gene rearrangement as shown by Southern blot procedures.

TABLE IV

DETECTION OF LYMPHOMA IN PERIPHERAL BLOOD BY THE PCR TECHNIQUE IN COMPLETE RESPONDERS CLINICAL OUTCOME ACCORDING TO RESULTS OF PCR ASSAY

| RESULTS OF PCR ASSAY | NUMBER OF PATIENTS | OUTCOME RELAPSE | REMISSION |
|---|---|---|---|
| POSITIVE | 4 | 3 | 1 |
| NEGATIVE | 1 | 0 | 1 |

The remaining one patient is still in remission while on maintenance therapy. The only one patient whose remission blood sample was negative has been in continuous remission for more than 20 months. Since the pretreatment sample was amplifiable in this patient, possible explanations for the remission sample being negative may be that either the number of neoplastic cells was too small to be detected or the patient was completely free of tumor.

The feasibility of using the PCR technique to detect minimal numbers of neoplastic cells carrying a chromosomal translocation was established by the methods of the present invention. Detection of small numbers of circulating monoclonal B cells by flow cytometry or clonal immunoglobulin gene rearrangement in patients with follicular lymphoma in remission has been reported (1,17). The sensitivity of the methods of the present invention far exceeds the sensitivity limit achieved by conventional Southern blot analysis or the flow cytometric method. Detection of minimal neoplastic cells with chromosomal translocation by means of PCR will make it possible to address several important biological and clinical questions that could not be answered before. For example, do patients in long term remission have quiescent tumor cells with proliferative potential? Can detection of minimal residual tumor cells predict early relapse? Do patients with persistent minimal residual disease after prolonged treatment require non-cross resistant therapy to prevent relapse? The answers will help in understanding tumor biology and designing strategies for cancer treatment.

The following cited articles are incorporated by reference herein for the reason cited.

CITED ARTICLES

1. E Hu et al., Lancet II, 1092 (1985).
2. ML Cleary, J Chao, R Warnke, J Sklar, Proc. Natl. Acad. Bci. USA, 81:593 (1984).
3. S Fukuhara, JD Rowley, D Variakojis, HM Golomb, Cancer Res., 39:3119 (1979).
4. J Yunis et al., N. Engl. J. Med., 307:1231 (1982).
5. CD Bloomfield et al., Cancer Res., 43:2975 (1983).
6. Y Tsujimoto et al., Science, 226:1097 (1984).
7. Y Tsujimoto et al., ibid, 228:1440 (1985).
8. A Bakhshi et al., Cell, 41:899 (1985).
9. MS Lee et al., Blood, 70:90 (1987).
10. ML Cleary, J Sklar, Proc. Natl. Acad. Sci. USA, 82:7439 (1985).
11. ML Cleary, SD Smith, J Sklar, Cell, 47:19 (1986).
12. Y Tsujimoto, J Gorham, J Cossman, E Jaffe, CM Croce, Science, 229:1390 (1985).
13. Y Tsujimoto, CM Croce, Proc. Natl. Acad. Sci. USA, 83:5214 (1986).
14. RK Saiki et al., Science, 230:1350 (1985).
15. JV Ravetch, U Siebenlist, S Korsmeyer, T Waldman, P Leder, Cell, 27:583 (1981).
16. Weiss et al., N. Engl. J. Med., 317:1185
17. BR Smith et al., N. Engl. J. Med., 311:1476 (1984).

Changes may be made in the operation and arrangement of the various elements, steps and procedures described herein without departing from the concept and scope of the invention as defined in the following claims.

What is claimed is:

1. A method for detecting neoplastic cells in an individual, said neoplastic cells being characterized by a t(14;18) chromosomal translocation related to a specific breakpoint clustering region, the method comprising the steps of:

incubating a mixture comprising deoxyribonucleotide triphosphates, DNA from a cell sample of the individual, DNA polymerase, a first oligonucleotide primer and a second oligonucleotide primer, consisting essentially of base sequence 5'-TTTGACCTTTAG-3' or an oligonucleotide competing with said first primer for hybridizing to at least a portion of (−)-strand DNA of chromosome 18q21 immediately 5' to a molecular breakpoint hot spot region located in exon 3 and said second primer consisting essentially of base sequence 3'-CAGAGGAGTCCA-5' or an oligonuleotide competing with said second primer for hybridizing to a sequence 3' to an end of segment $J_H$ of chromosome 14 immunoglobulin heavy chain gene wherein is located a breakpoint clustering region, said incubating promoting annealing of the primers to the translocation crossover site and synthesis of coding or non-coding translocation DNA sequences and a substantial portion of flanking DNA sequences, the incubation then being terminated by DNA denaturation;

repeating said incubation step without adding further cell sample in a cyclic manner to facilitate duplication of the original and newly synthesized translocated and substantial flanking DNA sequences, said repeating being carried out in a manner exponentially amplifying DNA sequences between and including DNA regions complementary to the first and second oligonucleotide primers; and analyzing the exponentially amplified DNA for oligonucleotide sequences characterizing the translocation region by separating the exponentially amplified DNA and hybridizing the amplified DNA with the first and second primers and identifying neoplastic cells by the presence of said sequences.

2. A method for detecting a t(14;18) translocation in neoplastic cells in an individual, said translocation derived from region J of chromosome 14 immunoglobulin heavy chain gene, the method comprising the steps of:

incubating a mixture comprising deoxyribonucleotide triphosphates, a DNA sample from tissue or cells of the individual, DNA polymerase and at least one set of oligonucleotide primers, each set of oligonucleotide primers consisting of a first oligonucleotide primer and a second oligonucleotide primer, said first oligonucleotide primer consisting essentially of base sequence 5'-TTTGACCTTTAG-3' or an oligonucleotide competing with said first primer for hybridizing to (−)-strand DNA of chromosome 18q21 within 1000 base pairs 5' to mbr and said second primer consisting essentially of base sequence 3'-CAGAGGAGTCCA-5' or an oligonucleotide competing with said second primer for hybridizing to a sequence 3' to the immunoglobulin heavy chain chromosome 14 $J_H$ region breakpoint said incubating being under conditions promoting annealing of the primers to the crossover sites of the translocation, the incubation then being terminated by DNA denaturation;

repeating said incubation step without further adding of cell sample in a cyclic manner to facilitate further synthesis of the original DNA and of newly synthesized DNA, said repeating being carried out in a manner facilitating repeated primer extensions and exponential amplification of DNA sequences at the crossover sites of the translocations;

separating amplified DNA by fractionation means;

hybridizing the exponentially amplified DNA with a probe wherein the probe base sequence is identical to at least a portion of 18q21(+) at a point 3' to the first primer; and analyzing the hybridized exponentially amplified DNA for the presence of oligonucleotide sequences characterizing the t(14;18) translocation region and identifying therefrom the presence of neoplastic cells by the presence of said sequences.

3. The method of claim 1 wherein the first and second primer nucleotide sequences are located within about 1000 bases from the nearest breakpoint clustering region.

4. The method of claim 1 wherein the oligonucleotide primers are each defined further as being from between about 12 and about 20 nucleotides in length.

5. The method of claim 1 wherein there is a single breakpoint clustering region.

6. The method of claim 1 or 2 wherein the translocation is defined further as involving a t(14;18) translocation.

7. The method of claim 2 wherein there are two or more breakpoint clustering regions to be analyzed.

8. The method of claim 2 wherein there is a major breakpoint clustering region and a minor breakpoint clustering region.

9. The method of claim 8 wherein said major breakpoint clustering region is the mbr region and said minor breakpoint clustering region being the mcr region.

10. The method of claim 2 wherein there are at least two breakpoint regions to be analyzed, two sets of oligonucleotide primers are added to the mixture and the probing is defined further as involving probes with sequences derived from the crossover sites of the translocated DNAs.

11. The method of claim 1 or 2 wherein the probing step is defined further as involving Southern blot analysis.

12. The method of claim 1 or 2 wherein the incubating step is followed by a terminating step and these steps are repeated from about 20 to about 50 times to exponentially amplify DNA flanked by oligonucleotide primers.

13. The method of claim 1 or claim 2 wherein the extension of a primer includes synthesis of translocation sequences and a substantial flanking DNA region including that nucleotide sequence complementary to the other primer.

14. The method of claim 12 wherein the terminating step involves denaturation of DNA templates.

15. The method of claim 1 or 2 wherein the neoplasm is human follicular lymphoma.

16. The method of claim 1 or 2 wherein the neoplasm is a non-Hodgkin's lymphoma.

17. The method of claim 1 or 2 wherein the neoplasm is a B-cell lymphoma.

18. The method of claim 1 or 2 wherein the neoplasm is a large cell lymphoma, a diffuse large cell lymphoma, a small noncleaved cell lymphoma, a B-cell leukemia or a Pre-B-cell leukemia.

19. The method of claim 1 or 2 wherein the cell sample of the individual comprises neoplastic cells.

20. The method of claim 1 or 2 wherein the deoxynucleotide phosphates include deoxyadenosine triphosphate, deoxythymidine triphosphate, deoxycytosine triphosphate and deoxyguanosine triphosphate.

21. The method of claim 1 or 2 wherein the DNA polymerase is the Klenow fragment of E. coli DNA polymerase or Thermus aquaticus DNA polymerase.

22. The method of claim 1 or 2 wherein the primers are at about 1 micromolar concentration.

23. The method of claim 1 or 2 wherein the chromosomal translocation is characterized by the breakpoints at both chromosome clustering within several hundred base pairs.

24. The method of claim 1 wherein the first primer is identical to sequences of chromosome 18q21(+) and wherein said sequences are 5' to or in the mbr region.

25. The method of claim 1 wherein the second primer is complementary to sequences in each (+)-strand J segment occurring in the immunoglobulin heavy chain at the 3' end.

26. The method of claim 2 wherein the probe has the sequence 5'-CACAGACCCACCCAGAGCCC-3'.

* * * * *

UNITED STATES PATENT AND TRADEMARK OFFICE
CERTIFICATE OF CORRECTION

PATENT NO. : 5,024,934
DATED : June 18, 1991
INVENTOR(S) : Ming-sheng Lee

It is certified that error appears in the above—identified patent and that said Letters Patent is hereby corrected as shown below:

In the Abstract at line 1, replace "related" with --relates--.

At col. 1, line 8, insert word --High-- before word "frequency".

At col. 1, line 9, insert --.-- after word "treatment".

At col. 1, line 20, insert --.-- after word "rearrangement".

At col. 5, line 54, replace "(+)" with --(±)--.

At col. 11, line 68, replace "Bci." with --Sci.--.

In claim 1, col. 12, at line 36, insert --said first primer-- before "consisting" and after "second nucoligonucleotide primer,".

Signed and Sealed this

First Day of December, 1992

*Attest:*

DOUGLAS B. COMER

*Attesting Officer*      *Acting Commissioner of Patents and Trademarks*